(12) United States Patent
Nair et al.

(10) Patent No.: US 10,407,739 B2
(45) Date of Patent: Sep. 10, 2019

(54) **DETECTION OF METHICILLIN-RESISTANT *STAPHYLOCOCCUS AUREUS* IN BIOLOGICAL SAMPLES**

(71) Applicant: QUEST DIAGNOSTICS INVESTMENTS INCORPORATED, Wilmington, DE (US)

(72) Inventors: Lakshmi Nair, Linda, CA (US); Heather Vincent, Carrboro, NC (US); Huong Mai, Irvine, CA (US); Michael Aye, Huntington Beach, CA (US); Michelle Tabb, Santa Ana, CA (US); Maurice Exner, San Juan Capistrano, CA (US)

(73) Assignee: QUEST DIAGNOSTICS INVESTMENTS INCORPORATED, Wilmington, DE (US)

( * ) Notice: Subject to any disclaimer, the term of this patent is extended or adjusted under 35 U.S.C. 154(b) by 702 days.

(21) Appl. No.: 14/490,845

(22) Filed: Sep. 19, 2014

(65) Prior Publication Data

US 2015/0087545 A1  Mar. 26, 2015

Related U.S. Application Data

(60) Provisional application No. 61/881,234, filed on Sep. 23, 2013.

(51) Int. Cl.
*C12Q 1/689* (2018.01)
*G01N 21/64* (2006.01)

(52) U.S. Cl.
CPC ......... *C12Q 1/689* (2013.01); *G01N 21/6428* (2013.01); *C12Q 2600/112* (2013.01); *C12Q 2600/158* (2013.01); *C12Q 2600/16* (2013.01); *G01N 2021/6432* (2013.01); *G01N 2021/6441* (2013.01)

(58) Field of Classification Search
None
See application file for complete search history.

(56) References Cited

U.S. PATENT DOCUMENTS

| | | | |
|---|---|---|---|
| 6,117,986 A | 9/2000 | Nardone et al. | |
| 2009/0035780 A1 | 2/2009 | McCarthy et al. | |
| 2011/0312504 A1* | 12/2011 | Driebe | C12Q 1/689 506/2 |
| 2012/0058481 A1* | 3/2012 | Ge | C12Q 1/6818 435/6.12 |
| 2012/0165229 A1 | 6/2012 | Reiske et al. | |
| 2013/0164752 A1 | 6/2013 | Pallier et al. | |
| 2016/0230216 A1 | 8/2016 | Nair et al. | |

FOREIGN PATENT DOCUMENTS

| | | |
|---|---|---|
| WO | WO 2009/135832 A1 | 11/2009 |
| WO | WO 2010/121298 A1 | 10/2010 |
| WO | WO 2013/048583 A2 | 4/2013 |
| WO | WO 2013/110660 A1 | 8/2013 |

OTHER PUBLICATIONS

Mackay, I.M. Clinical Microbiology and Infection 2004; 10: 190-212.*
Valasek et al. Advances in Physiology Education 2005; 29: 151-159.*
Palavecino, E. L. Methods in Molecular Biology 2014; 1085: 71-83.*
Larssen et al. Clinical Microbiology and Infection 2008; 14: 611-614 (Year: 2008).*
Whitcombe et al. Nature Biotechnology 1999; 17: 804-807 (Year: 1999).*
Oliveira et al. Antimicrobial Agents and Chemotherapy 2002; 46: 2155-2161 (Year: 2002).*
GenBank Accession No. AB035454.1 for the *Staphylococcus aureus* hlgA, orfX, spa genes, partial and complete cds, Jul. 26, 2016 [online], [retrieved on Aug. 17, 2018], retrieved from the Internet: <URL: www.ncbi.nlm.nih.gov/nuccore/ab035454.1 >. (Year: 2016).*
Becker et al., "Evaluation of a Modular Multiplex-PCR Methicillin-Resistant *Staphylococcus aureus* Detection Assay Adapted for mecC Detection," J. Clin. Microbiol., vol. 51, No. 6, pp. 1917-1921, Mar. 20, 2013.
Petersen et al., Epidemiology of methicillin-resistant *Staphylococcus aureus* carrying the novel mecC gene in Denmark corroborates a zoonotic reservoir with transmission to humans, Clinical Microbiology and Infection, vol. 19, Issue 1, pp. 16-22, Oct. 19, 2012.
Paterson et al., "The emergence of mecC methicillin-resistant *Staphylococcus aureus*," Trends in Microbiology, vol. 22, No. 1, pp. 42-47, Jan. 2014.
International Search Report dated Jan. 9, 2015 in application No. PCT/US2014/056777.
Supplementary European Search Report dated Apr. 6, 2017, in EP 14845976.1.
Medhus et al., "Methicillin-resistant *Staphylococcus aureus* with the novel mecC gene variant isolated from a cat suffering from chronic conjunctivitis," J. Antimicrob. Chemother., Dec. 4, 2012, 0:1-2.
Pichon et al., "Development of a real-time quadruplex PCR assay for simultaneous detection of nuc, Panton-Valentine leucocidin (PVL), mecA and homologue mecA$_{LGA251}$," J. Antimicrob. Chemother., Jun. 11, 2012, 67(10):2338-2341.
Stegger et al., "Rapid detection, differentiation and typing of methicillin-resistant *Staphylococcus aureus* harbouring either mecA or the new mecA homologue mecA$_{LGA251}$," Clinical Microbiology and Infection, Nov. 7, 2011, 18(4):395-400.

(Continued)

Primary Examiner — Angela M. Bertagna
(74) Attorney, Agent, or Firm — Foley & Lardner LLP

(57) ABSTRACT

Disclosed are methods of identifying a methicillin-resistant *Staphylococcus aureus* (MRSA) in a sample wherein the methods involve detecting a *S. aureus*-specific nucleic acid sequence, mecA and mecC, in the sample. Kits for determining the presence of MRSA in a sample are also provided.

17 Claims, No Drawings

Specification includes a Sequence Listing.

(56) References Cited

OTHER PUBLICATIONS

English translation of Office Action dated Aug. 14, 2018, in JP 2016-516533.
Office Action dated Jul. 12, 2018, in U.S. Appl. No. 15/024,167.
Notice of Allowance dated Apr. 2, 2019, in U.S. Appl. No. 15/024,167.
Office Action dated Jan. 18, 2019, in U.S. Appl. No. 15/024,167.

* cited by examiner

SEQUENCE LISTING

```
<160> NUMBER OF SEQ ID NOS: 12

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cttgataaaa agcattttgt tgagcttca                                       29

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      primer-probe

<400> SEQUENCE: 2
agcggtgcag caggtgttac gccaccgct                                       29

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 3
tgcatctgta actttaggta catta                                              25

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcaccgattc ccaaatcttg c                                                  21

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      primer-probe

<400> SEQUENCE: 5
acgtgcctaa tgctaatgca atgcgggcac gt                                      32

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aagcaagcaa tagaatcatc agaca                                              25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcttcaccaa cacctagttt tttca                                              25

<210> SEQ ID NO 8
<211> LENGTH: 44
<212> TYPE: DNA
<213> ORGANISM: Artificial Sequence
<220> FEATURE:
<223> OTHER INFORMATION: Description of Artificial Sequence: Synthetic
      primer-probe

<400> SEQUENCE: 8
acgcggcctt actgcctaat tcgagtgcta ctctagcgcc gcgt                         44

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 9
ggtaatatcg acttaaaaca agcaataga                                            29

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer-probe

<400> SEQUENCE: 10
tgcatctgta actttaggta catta                                                25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer-probe

<400> SEQUENCE: 11
aagcaagcaa tagaatcatc agaca                                                25

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      primer-probe

<400> SEQUENCE: 12
ggtaatatcg acttaaaaca agcaataga                                            29
```

DETECTION OF METHICILLIN-RESISTANT *STAPHYLOCOCCUS AUREUS* IN BIOLOGICAL SAMPLES

RELATED APPLICATIONS

The instant application claims benefit under 35 U.S.C. 119(e) of U.S. Provisional Application 61/881,234, filed Sep. 23, 2013.

SEQUENCE LISTING

The instant application contains a Sequence Listing which has been submitted electronically in ASCII format on Dec. 1, 2014, in ASCII format and is hereby incorporated by reference in its entirety. Said ASCII copy, created on Nov. 26, 2014, is named seqlisting.txt and is 4 KB in size.

FIELD OF THE INVENTION

The present invention relates generally to methods of pathogen detection. In particular, the present invention relates to methods of detecting *Staphylococcus aureus* and methicillin-resistant *Staphylococcus aureus* (MRSA) in a biological sample.

BACKGROUND OF THE INVENTION

The following description is provided to assist the understanding of the reader. None of the information provided or references cited is admitted to be prior art to the present invention.

*Staphylococcus aureus* (*S. aureus*) is a cause of a variety of conditions in humans, including skin infections (e.g. folliculitis, styes, cellulitis, impetigo, and furunculosis), pneumonia, mastitis, phlebitis, meningitis, scalded skin syndrome, osteomyelitis, urinary tract infections, and food poisoning. In addition, the Centers for Disease Control and Prevention (CDC) has recognized methicillin-resistant *S. aureus* (MRSA) as a growing problem in the healthcare setting as it is one of the major causes of hospital acquired infections such as hospital-acquired (HA or nosocomial) infection of surgical wounds.

MRSA is one of the two most rampant antibiotic resistant pathogens; vancomycin-resistant enterococcus is the other (Society for Healthcare and Epidemiology, SHEA guidelines 2003). Over 50% of nosocomial infections in intensive care units are due to MRSA (National Nosocomial Infections Surveillance System, NNIS report, January 1992-June 2004). Accordingly, MRSA represents a significant threat to public health.

Methicillin resistance is caused by the acquisition of an exogenous gene mecA that encodes penicillin-binding protein (PBP2a or PBP2'), which exhibits a low affinity for β-lactam antibiotics (Wielders and Fluit, 2002). mecA is carried on a mobile genetic element called Staphylococcal cassette chromosome mec (SCCmec) which also contains the ccr gene complex encoding the recombinases necessary for the element's mobility. The SCCmec cassette is a large element that can move in and out of the *S. aureus* genome.

The mecA gene also is found in coagulase-negative *Staphylococcus* (CNS) strains that are less pathogenic than *S. aureus*. These strains include *S. epidermidis*, *S. haemolyticus*, *S. saprophyticus*, *S. capitis*, *S. warneri*, *S. sciuri* and *S. caprae*. Some of these other strains of *Staphylococcus* inhabit the same environments as *S. aureus* such as the anterior nares and the skin. It follows that clinical samples such as nasal swabs or wound swabs could potentially contain a mixture of more than one Staphylococcal species. Therefore, detection of mecA alone is not sufficient to identify MRSA directly from clinical sample. Because identification of MRSA is of greater clinical significance than the other *Staphylococcus* species due to its increased pathogenicity and toxicity, it is desirable to have a diagnostic assay that distinguishes MRSA from the other staphylococcal strains containing the mecA gene.

More recently, an additional mec gene, named mecC, was discovered which also confers beta-lactam resistance. mecC (GenBank accession no. FR821779), formerly referred to as mecA homologue in early publications, is present on a SCCmec XI element (GenBank accession no. FR823292). The mecC gene has been described in human and bovine *S. aureus* and it encodes a protein that has <63% aa identity with PBP2a encoded by mecA.

Hospital acquired (HA) MRSA is typically controlled by monitoring patients and personnel for infection. Contact precautions and/or patient isolation may be appropriate when an infection develops or to prevent infections to individuals particularly at risk. The prevalence of community acquired (CA) MRSA is also increasing. CA-MRSA is defined as MRSA acquired in persons with no known risk factors for MRSA infection (e.g. recent hospitalization, contact with infected patient). Because a quick and reliable identification of MRSA has become important for the diagnosis and treatment of infected patients, as well as for implementation and management of hospital infection control procedures, it is desirable to have a diagnostic assay that detects the presence of *S. aureus* and, in particular, the presence of MRSA. It is additionally desirable to have such an assay that does not require a front-end specimen preparation process separate from the detection system.

SUMMARY OF THE INVENTION

Provided herein are methods and kits for detecting MRSA in a biological sample. In particular, the described methods relate to the positive identification of MRSA by screening for the presence of three marker nucleic acid sequences. The present methods may be practiced on unprocessed biological samples, resulting in a direct, streamlined sample-to-answer process.

The disclosed method for determining the presence or absence of methicillin resistant *Staphylococcus aureus* (MRSA) in a biological sample comprises:
 (a) contacting the biological sample with:
  (i) a first primer pair that specifically hybridizes under stringent conditions to a target nucleic acid specific for *Staphylococcus aureus*, if present,
  (ii) a second primer pair that specifically hybridizes under stringent conditions to a target mecC nucleic acid, if present, and
  (iii) a third primer pair that specifically hybridizes under stringent conditions to a target mecAC nucleic acid, if present,
 to produce a reaction-sample mixture, wherein at least one primer of each primer pair is associated with a fluorophore label,
 (b) subjecting the reaction-sample mixture to real-time polymerase chain reaction (PCR) conditions under which each of the target nucleic acids present in the biological sample is amplified to produce a fluorescent signal,
 (c) measuring the amount of fluorescent signal produced by each fluorophore, and (d) determining the presence or absence of MRSA by comparing the cycle threshold of the target nucleic acids, whereby
  (i) MRSA is determined to be present in the biological sample when a fluorescent signal is detected for both the *S. aureus* specific nucleic acid and the mecA and/or mecC nucleic acids and
    (1) the cycle threshold (Ct) from the *S. aureus* specific nucleic acid minus the Ct from the mecA and/or mecC nucleic acids≤1.9, or
    (2) the Ct from the *S. aureus* specific nucleic acid minus the Ct from the mecA and/or mecC nucleic acids>1.9 and the Ct from the mecA and/or mecC nucleic acids plus 1.9<Ct from the *S. aureus* specific nucleic acid;
  (ii) *S. aureus* and a methicillin resistance gene are determined to be present in the biological sample when a fluorescent signal is detected for both the *S. aureus* specific nucleic acid and the mecA and/or mecC nucleic acids, and the Ct from the *S. aureus* specific nucleic acid minus the Ct from the mecA and/or mecC nucleic acids<1.9, and the Ct from the *S. aureus* specific nucleic acid plus 1.9<the Ct from the mecA and/or mecC nucleic acids; or
  (iii) *S. aureus* is determined to be present and MRSA is determined to be absent in the biological sample if a fluorescent signal is detected for the *S. aureus* specific target nucleic acid but no fluorescent signal is detected for mecA and/or mecC.

All primer pairs may be contained together in an amplification master mix further comprising DNA polymerase, dNTPs and PCR buffer prior to contacting with the biological sample. In addition, the amplification master mix may further comprise a fourth primer pair that specifically hybridizes under stringent conditions to a control target nucleic acid.

In some embodiments, the target nucleic acid specific for *Staphylococcus aureus* comprises all or a portion of a gene sequence selected from the group consisting of: spa, agr, ssp protease, sir, sodM, cap, coa, alpha hemolysin, gamma hemolysin, femA, Tuf, sortase, fibrinogen binding protein, clfB, srC, sdrD, sdrE, sdrF, sdrG, sdrH, NAD synthetase, sar, sbi, rpoB, gyrase A, and orfX. In a specific embodiment, the target nucleic acid specific for *Staphylococcus aureus* is spa.

The first primer pair may be directed against the spa nucleic acid sequence and consist of a first primer comprising SEQ ID NO:1 and a second primer comprising SEQ ID NO: 2. The second primer pair, which is directed to the mecC nucleic acid sequence, may consist of a first primer comprising SEQ ID NO:4 and a second primer comprising SEQ ID NO:6. The third primer pair, which is directed to mecA nucleic acid, may consist of a first primer comprising SEQ ID NO:7 and a second primer comprising SEQ ID NO:9.

One primer of each primer pair may comprise a probe sequence element as part of the same primer molecule, resulting in what is referred to as a primer-probe (e.g. a Scorpion™ primer-probe). The probe sequence typically is located at the 5' end of the primer and further may comprises a fluorophore associated with a quencher to reduce background fluorescence. Following PCR extension, the synthesized target region is attached to the same strand as the probe. Upon denaturation, the probe portion of the Scorpion™ specifically hybridizes to a part of the newly produced PCR product, physically separating the fluorophore from the quencher, thereby producing a detectable signal. In some embodiments, the fluorophore of the mecA primer and the fluorophore of the mecC primer are identical. The fluorophore of the primer-probes may be a fluorescein amidite (FAM) and the fluorophore of the mecA and mecC spa gene may be a xanthene dye that fluoresces in the red region of the visible spectrum.

The biological sample may be brought into contact with one or more of the primer pairs separately or simultaneously. Where the contact occurs simultaneously (i.e. multiplexing), one or more of the first, second, and third primer pairs are brought into contact with the biological sample and with each other to amplify the target nucleic acid sequences. Optionally, an internal positive control nucleic acid and a fourth primer pair complementary to the internal positive control nucleic acid may be included in the amplification mixture.

Kits comprising oligonucleotides which may be primers or primer-probes for performing amplifications as described herein also are provided.

DETAILED DESCRIPTION OF THE INVENTION

The present invention is described herein using several definitions, as set forth below and throughout the specification.

As used herein, unless otherwise stated, the singular forms "a," "an," and "the" include plural reference. Thus, for example, a reference to "an oligonucleotide" includes a plurality of oligonucleotide molecules, and a reference to "a nucleic acid" is a reference to one or more nucleic acids.

As used herein, "about" means plus or minus 10%.

A primer pair that specifically hybridizes under stringent conditions to a target nucleic acid may hybridize to any portion of the gene. As a result, the entire gene may be amplified or a segment of the gene may be amplified, depending on the portion of the gene to which the primers hybridize.

The terms "amplification" or "amplify" as used herein include methods for copying a target nucleic acid, thereby increasing the number of copies of a selected nucleic acid sequence. Amplification may be exponential or linear. A target nucleic acid may be DNA (such as, for example, genomic DNA and cDNA) or RNA. The sequences amplified in this manner form an "amplicon." While the exemplary methods described hereinafter relate to amplification using the polymerase chain reaction (PCR), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in PCR Protocols, Innis et al., Eds., Academic Press, San Diego, Calif. 1990, pp 13-20; Wharam, et al., Nucleic Acids Res. 2001 Jun. 1; 29(11):E54-E54; Hafner, et al., Biotechniques 2001 April; 30(4):852-860.

The terms "complement," "complementary," or "complementarity" as used herein with reference to polynucleotides (i.e., a sequence of nucleotides such as an oligonucleotide or a target nucleic acid) refer to standard Watson/Crick pairing rules. The complement of a nucleic acid sequence such that the 5' end of one sequence is paired with the 3' end of the other, is in "antiparallel association." For example, the sequence "5'-A-G-T-3'" is complementary to the sequence "3'-T-C-A-S'." Certain bases not commonly found in natural nucleic acids may be included in the nucleic acids described herein; these include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be a sequence of RNA complementary to the DNA sequence or its complement sequence, and can also be a cDNA. The term "substantially complementary" as used herein means that two sequences specifically hybridize (defined below). The skilled artisan will understand that substantially complementary sequences need not hybridize along their entire length. A nucleic acid that is the "full complement" or that is "fully complementary" to a reference sequence consists of a nucleotide sequence that is 100% complementary (under Watson/Crick pairing rules) to the reference sequence along the entire length of the nucleic acid that is the full complement. A full complement contains no mismatches to the reference sequence.

As used herein, the term "detecting" used in context of detecting a signal from a detectable label to indicate the presence of a target nucleic acid in the sample does not require the method to provide 100% sensitivity and/or 100% specificity. As is well known, "sensitivity" is the probability that a test is positive, given that the person has a target nucleic acid, while "specificity" is the probability that a test is negative, given that the person does not have the target nucleic acid. A sensitivity of at least 50% is preferred, although sensitivities of at least 60%, at least 70%, at least 80%, at least 90% and at least 99% are clearly more preferred. A specificity of at least 50% is preferred, although sensitivities of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

A "fragment" in the context of a nucleic acid refers to a sequence of nucleotide residues which are at least about 5 nucleotides, at least about 7 nucleotides, at least about 9 nucleotides, at least about 11 nucleotides, or at least about 17 nucleotides. The fragment is typically less than about 300 nucleotides, less than about 100 nucleotides, less than about 75 nucleotides, less than about 50 nucleotides, or less than 30 nucleotides. In certain embodiments, the fragments can be used in polymerase chain reaction (PCR), various hybridization procedures or microarray procedures to identify or amplify identical or related parts of mRNA or DNA molecules. A fragment or segment may uniquely identify each polynucleotide sequence of the present invention.

"Genomic nucleic acid" or "genomic DNA" refers to some or all of the DNA from a chromosome. Genomic DNA may be intact or fragmented (e.g., digested with restriction endonucleases by methods known in the art). In some embodiments, genomic DNA may include sequence from all or a portion of a single gene or from multiple genes. In contrast, the term "total genomic nucleic acid" is used herein to refer to the full complement of DNA contained in the genome. Methods of purifying DNA and/or RNA from a variety of samples are well-known in the art.

The term "multiplex PCR" as used herein refers to simultaneous amplification of two or more products within the same reaction vessel. Each product is primed using a distinct primer pair. A multiplex reaction may further include specific probes for each product, that are labeled with detectable moieties.

As used herein, the term "oligonucleotide" refers to a short polymer composed of deoxyribonucleotides, ribonucleotides or any combination thereof. Oligonucleotides are generally at least about 10, 11, 12, 13, 14, 15, 20, 25, 40 or 50 up to about 100, 110, 150 or 200 nucleotides (nt) in length, more preferably from about 10, 11, 12, 13, 14, or 15 up to about 70 or 85 nt, and most preferably from about 18 up to about 26 nt in length. The single letter code for nucleotides is as described in the U.S. Patent Office Manual of Patent Examining Procedure, section 2422, table 1. In this regard, the nucleotide designation "R" means purine such as guanine or adenine, "Y" means pyrimidine such as cytosine or thymidine (uracil if RNA); and "M" means adenine or cytosine. An oligonucleotide may be used as a primer or as a probe.

As used herein, a "primer" for amplification is an oligonucleotide that is complementary to a target nucleotide sequence and leads to addition of nucleotides to the 3' end of the primer in the presence of a DNA or RNA polymerase. The 3' nucleotide of the primer should generally be identical to the target nucleic acid sequence at a corresponding nucleotide position for optimal expression and amplification. The term "primer" as used herein includes all forms of primers that may be synthesized including peptide nucleic acid primers, locked nucleic acid primers, phosphorothioate modified primers, labeled primers, and the like. As used herein, a "forward primer" is a primer that is complementary to the anti-sense strand of dsDNA. A "reverse primer" is complementary to the sense-strand of dsDNA. An "exogenous primer" refers specifically to an oligonucleotide that is added to a reaction vessel containing the sample nucleic acid to be amplified from outside the vessel and is not produced from amplification in the reaction vessel. A primer that is "associated with" a fluorophore or other label is connected to label through some means. An example is a primer-probe.

Primers are typically from at least 10, 15, 18, or 30 nucleotides in length up to about 100, 110, 125, or 200 nucleotides in length, preferably from at least 15 up to about 60 nucleotides in length, and most preferably from at least 25 up to about 40 nucleotides in length. In some embodiments, primers and/or probes are 15 to 35 nucleotides in length. There is no standard length for optimal hybridization or polymerase chain reaction amplification. An optimal length for a particular primer application may be readily determined in the manner described in H. Erlich, PCR Technology, Principles and Application for DNA Amplification, (1989).

A "primer pair" is a pair of primers that are both directed to target nucleic acid sequence. A primer pair contains a forward primer and a reverse primer, each of which hybridizes under stringent condition to a different strand of a double-stranded target nucleic acid sequence. The forward primer is complementary to the anti-sense strand of the dsDNA and the reverse primer is complementary to the sense-strand. One primer of a primer pair may be a primer-probe (i.e., a bi-functional molecule that contains a PCR primer element covalently linked by a polymerase-blocking group to a probe element and, in addition, may contain a fluorophore that interacts with a quencher).

An oligonucleotide (e.g., a probe or a primer) that is specific for a target nucleic acid will "hybridize" to the target nucleic acid under specified conditions. As used herein, "hybridization" or "hybridizing" refers to the process by which an oligonucleotide single strand anneals with a complementary strand through base pairing under defined hybridization conditions.

"Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point (Tm) for the specific sequence at a defined ionic strength and pH. The Tm is the temperature (under defined ionic strength and pH) at which 50% of the target nucleic acid hybridizes to a perfectly matched probe. Equations for calculating Tm and conditions for nucleic acid hybridization are known in the art. Specific hybridization preferably occurs under stringent conditions, which are well known in the art. Stringent hybridization conditions are hybridization in 50% formamide, 1 M NaCl, 1% SDS at 37° C., and a wash in 0.1×SSC at 60° C. Hybridization procedures are well known in the art and are described in e.g. Ausubel et al, Current Protocols in Molecular Biology, John Wiley & Sons Inc., 1994.

As used herein, an oligonucleotide is "specific" for a nucleic acid if the oligonucleotide has at least 50% sequence identity with the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity. Sequence identity can be determined using a commercially available computer program with a default setting that employs algorithms well known in the art. As used herein, sequences that have "high sequence identity" have identical nucleotides at least at about 50% of aligned nucleotide positions, preferably at least at about 60% of aligned nucleotide positions, and more preferably at least at about 75% of aligned nucleotide positions.

Oligonucleotides used as primers or probes for specifically amplifying (i.e., amplifying a particular target nucleic acid) or specifically detecting (i.e., detecting a particular target nucleic acid sequence) a target nucleic acid generally are capable of specifically hybridizing to the target nucleic acid under stringent conditions.

As used herein, the term "sample" or "test sample" may comprise clinical samples, isolated nucleic acids, or isolated microorganisms. In preferred embodiments, a sample is obtained from a biological source (i.e., a "biological sample"), such as tissue, bodily fluid, or microorganisms collected from a subject. Sample sources include, but are not limited to, sputum (processed or unprocessed), bronchial alveolar lavage (BAL), bronchial wash (BW), blood, bodily fluids, cerebrospinal fluid (CSF), urine, plasma, serum, or tissue (e.g., biopsy material). Preferred sample sources include nasopharyngeal swabs, wound swabs, and nasal washes. The term "patient sample" as used herein refers to a sample obtained from a human seeking diagnosis and/or treatment of a disease.

An "amplification mixture" as used herein is a mixture of reagents that are used in a nucleic acid amplification reaction, but does not contain primers or sample. An amplification mixture comprises a buffer, dNTPs, and a DNA polymerase. An amplification mixture may further comprise at least one of MgCl2, KCl, nonionic and ionic detergents (including cationic detergents).

An "amplification master mix" comprises an amplification mixture and primers for amplifying a target nucleic acid, but does not contain a sample to be amplified.

An "reaction-sample mixture" as used herein refers to a mixture containing amplification master mix plus sample.

A "probe sequence element" as used herein refers to a stretch of nucleotides that is associated with a primer in that it is connected to or adjacent to the primer nucleic acid sequence, and that specifically hybridizes under stringent conditions to a target nucleic acid sequence to be detected.

As used herein, the term "primer-probe detection system" refers to a method for real-time PCR. This method utilizes a bi-functional molecule (referred to herein as a primer-probe), which contains a PCR primer element covalently linked by a polymerase-blocking group to a probe element. Additionally, each primer-probe molecule contains a fluorophore that interacts with a quencher to reduce the background fluorescence. Primer-probes, as used herein, may comprise a 3' primer with a 5' extended probe tail comprising a hairpin structure which possesses a fluorophore/quencher pair. During PCR, the polymerase is blocked from extending into the probe tail by the inclusion of hexethlyene glycol (HEG). During the first round of amplification the 3' target-specific primer anneals to the target nucleic acid and is extended such that the primer-probe is now incorporated into the newly synthesized strand, which possesses a newly synthesized target region for the 5' probe. During the next round of denaturation and annealing, the probe region of the primer-probe hairpin loop will hybridize to the target, thus separating the fluorophore and quencher and creating a measurable signal. Such primer-probes are described in Whitcombe et al., Nature Biotech 17: 804-807 (1999). SCORPION primers are exemplary primer-probes.

The terms "target nucleic acid" "target nucleic acid sequence" or "target sequence" as used herein refer to a sequence which includes a segment of nucleotides of interest to be amplified and detected. Copies of the target sequence which are generated during the amplification reaction are referred to as amplification products, amplimers, or amplicons. Target nucleic acid may be composed of segments of a chromosome, a complete gene with or without intergenic sequence, segments or portions of a gene with or without intergenic sequence, or sequence of nucleic acids which probes or primers are designed. Target nucleic acids may include a wild-type sequence(s), a mutation, deletion or duplication, tandem repeat regions, a gene of interest, a region of a gene of interest or any upstream or downstream region thereof. Target nucleic acids may represent alternative sequences or alleles of a particular gene. Target nucleic acids may be derived from genomic DNA, cDNA, or RNA. As used herein target nucleic acid may be DNA or RNA extracted from a cell or a nucleic acid copied or amplified therefrom, or may include extracted nucleic acids further converted using a bisulfite reaction.

A "positive control nucleic acid" or "internal positive amplification control" as used herein is a nucleic acid known to be present in a sample at a certain amount or level. In some embodiments, a positive control nucleic acid is not naturally present in a sample and is added to the sample prior to subjecting the reaction-sample mixture to real-time polymerase chain reaction in the disclosed methods for determining the presence or absence MRSA. As used herein, a "cycle threshold" (Ct) for an analyte is the PCR cycle at which the fluorescence signal crosses a specified fluorescence threshold. The Ct depends on the amplification reaction efficiency which includes starting template copy number, organism lysis, PCR amplification, hybridization or cleavage of fluorogenic probe and sensitivity of detection.

As used herein "TaqMan® PCR detection system" refers to a method for real time PCR. In this method, a TaqMan® probe which hybridizes to the nucleic acid segment amplified is included in the amplification master mix. The TaqMan® probe comprises a donor and a quencher fluorophore on either end of the probe and in close enough proximity to each other so that the fluorescence of the donor is taken up by the quencher. However, when the probe hybridizes to the amplified segment, the 5'-exonuclease activity of the Taq polymerase cleaves the probe thereby allowing the donor fluorophore to emit fluorescence which can be detected.

The present inventors have discovered that a positive identification of MRSA can be made by determining the presence or absence of three marker nucleic acid sequences in a biological sample. Accordingly, the present invention provides methods of determining the presence or absence of methicillin resistant *Staphylococcus aureus* (MRSA) in a biological sample, the method comprising: (a) bringing the biological sample in contact with: a first primer pair that specifically hybridizes under stringent conditions to a target nucleic acid specific for *Staphylococcus aureus*, if present, a second primer pair that specifically hybridizes under stringent conditions to a target mecA nucleic acid if present, and a third primer pair that specifically hybridizes under stringent conditions to a target mecC nucleic acid, if present, to produce a reaction-sample mixture, wherein at least one primer of each primer pair is associated with a fluorophore label, (b) subjecting the reaction-sample mixture to real-time polymerase chain reaction (PCR) conditions under which each of the target nucleic acids present in the biological sample is amplified to produce a fluorescent signal, (c) measuring the amount of fluorescent signal produced by each fluorophore using a an integrated thermal cycling system, and (d) determining the presence or absence of MRSA by comparing the amount of fluorescence from the target nucleic acids and applying an algorithm discovered by the present inventors.

Biological Samples and Sample Preparation

Biological samples in which MRSA can be detected and quantified using the disclosed methods are from sterile and/or non-sterile sites. Sterile sites from which samples can be obtained are body fluids such as whole blood, plasma, cell free plasma, urine, cerebrospinal fluid, synovial fluid, pleural fluid, pericardial fluid, intraocular fluid, tissue biopsies or endotracheal aspirates. As used herein, "cell-free plasma" indicates plasma containing less than 1% cells by volume. Non-sterile sites from which samples can be taken are e.g. sputum, stool, swabs from e.g. skin, inguinal, nasal and/or throat. Preferably, samples from non-sterile sites, more preferably wound and/or nasal swabs are used in the present invention. Samples for MRSA detection may also comprise cultures of isolated bacteria grown on appropriate media to form colonies. Samples may also include bacterial isolates.

Exemplary biological samples sources include nasopharyngeal swabs, wound swabs, and nasal washes. A biological sample may be suspected of containing MRSA and/or MRSA nucleic acids. In addition, a biological sample may be obtained from an individual suspected of being infected with MRSA. The biological sample may be contacted with an amplification master mix for use in a microfluidic/microelectronic centrifugation platform.

Although the disclosed methods preferably employ unprocessed biological samples thus resulting in a direct, streamlined sample-to-answer process, the detection methods disclosed herein will be effective if used on isolated nucleic acid (DNA or RNA) purified from a biological sample according to any methods well known to those of skill in the art. If desired, the sample may be collected or concentrated by centrifugation and the like. The cells of the sample may be subjected to lysis, such as by treatments with enzymes, heat surfactants, ultrasonication or combination thereof. Alternatively, a biological sample may be processed using a commercially available nucleic acid extraction kit.

In some embodiments, one or more primer pairs are present in an amplification master mix that further comprises DNA polymerase, dNTPs and PCR buffer prior to contacting with the biological sample. Although the amplification preferably occurs in a multiplex format, individual reactions for each marker alternatively may be used. The biological sample may be contacted with the primer pair(s) and/or with an amplification master mix to form a reaction-sample mixture in a direct amplification disc. For example, the biological sample may be contacted with the amplification master mix in a direct amplification disc such as the Direct Amplification Disc marketed by Focus Diagnostics, Inc. (Cypress, Calif., USA) as part of the SIMPLEXA Direct real time PCR assays to work in concert with the 3M™ Integrated Cycler. A direct amplification disc is a thin, circular disc containing multiple designated regions, each of which contains a well for receiving an amplification master mix and an associated well for receiving unprocessed patient sample. The sample-reaction mixture is produced in the direct amplification disc upon or after addition of the amplification master mix and the sample.

Real-Time PCR

The reaction-sample mixture is subjected to real-time polymerase chain reaction (PCR) conditions under which each of the target nucleic acids present in the biological sample is amplified and the amplified product(s) are detected and measured. In some embodiments, the biological sample is loaded directly into a direct amplification disc without a separate, front-end specimen preparation, followed by RT-PCR detection and differentiation of target analytes in the same disc. Preferably, amplification is performed in a Direct Amplification Disc (an 8-well disc from Focus Diagnostics, Inc.). In some embodiments, real time PCR amplification is performed using the SIMPLEXA Direct assay in a direct amplification disc and detection is performed using an integrated thermalcycler such as the 3M™ Integrated Cycler sold by 3M (St. Paul, Minn., USA). The 3M™ Integrated Cycler can receive a Direct Amplification Disc and is capable of performing multiple assays per disc. This apparatus can heat at >5° C. per second and cool at >4° C. per second. Cycling parameters can be varied, depending on the length of the amplification products to be extended.

An internal positive amplification control (IPC) can be included in the sample, utilizing oligonucleotide primers, probes and/or primer-probes.

Accordingly, in some embodiments, at least one primer of each primer pair in the amplification reaction comprises a detectable moiety. The detectable moiety may be on a probe that is attached to the primer, such as with a primer-probe. The probe may be detectably labeled by methods known in the art. Useful labels include, e.g., fluorescent dyes (e.g., Cy5®, Cy3®, FITC, rhodamine, lanthamide phosphors, Texas red, fluorescein amidite (FAM), JOE, a xanthene dye such as Cal Fluor Red 610® ("CFR610") that fluoresces in the red region of the visible spectrum and can be effectively quenched by a I-BHQ2 dye, Quasar 670®, $^{32}$P, $^{35}$S, $^{3}$H, $^{14}$C, $^{125}$I, $^{131}$I, electron-dense reagents (e.g., gold), enzymes, e.g., as commonly used in an ELISA (e.g., horseradish peroxidase, beta-galactosidase, luciferase, alkaline phosphatase), colorimetric labels (e.g., colloidal gold), magnetic labels (e.g., Dynabeads™), biotin, dioxigenin, or haptens and proteins for which antisera or monoclonal antibodies are available. Other labels include ligands or oligonucleotides capable of forming a complex with the corresponding receptor or oligonucleotide complement, respectively. The label can be directly incorporated into the nucleic acid to be detected, or it can be attached to a probe (e.g., an oligonucleotide) or antibody that hybridizes or binds to the nucleic acid to be detected.

Thus, following amplification, the various target segments can be identified by using different detectable moieties such as size and/or color. The detectable moiety may be a fluorescent dye. In some embodiments, the different primer pairs are labeled with different distinguishable detectable moieties. Thus, for example, HEX and FAM fluorescent dyes may be present on different primers in the multiplex PCR and associated with the resulting amplicons. In other embodiments, the forward primer is labeled with one detectable moiety, while the reverse primer is labeled with a different detectable moiety, e.g. FAM dye for a forward primer and HEX dye for a reverse primer. Use of different detectable moieties is useful for discriminating between amplified products which are of the same length or are very similar in length. In some embodiments a primer-probe for the S. aureus specific gene is labeled with one detectable label (such as FAM) and a primer-probe specific for each of mecA and mecC genes is labeled with a different detectable label (such as CFR610). Thus, in certain embodiments, two different fluorescent dyes are used to label different primer-probes used in a single amplification.

In some embodiments, the probes employed are detectably labeled and the detecting is accomplished by detecting the probe label for each amplification product. A quencher may further be associated with the detectable label which prevents detection of the label prior to amplification of the probe's target. TAQMAN probes are examples of such probes.

In certain embodiments, the probe and one of the primers of the primer pair may constitute part of the same molecule. This is referred to as a primer-probe (e.g. a SCORPION primer-probe). In these embodiments, the primer-probe further contains a fluorophore associated with a quencher to reduce background fluorescence. Following PCR extension with such a fluorescent labeled primer-probes, the synthesized target region is attached to the same strand as the probe. Upon denaturation, the probe portion of the primer-probe specifically hybridizes to a part of the newly produced PCR product, physically separating the fluorophore from the quencher, thereby producing a detectable signal. Thus, in some embodiments, one primer of each primer pair may be a primer-probe that comprises a probe sequence element at the 5' end of a primer, wherein the probe element further comprises a fluorophore and a quencher.

In some embodiments, the probes employed in the disclosed methods comprise or consist of short fluorescently labeled DNA sequences designed to detect sections of DNA sequence with a genetic variation such as those disclosed in French et al. HyBeacon probes: a new tool for DNA sequence detection and allele discrimination, Mol Cell Probes, 2001 December; 15(6):363-74, incorporated by reference herein in its entirety. The central location of the fluorescent molecule within this type of probe provides certain advantages over probes that have signaling chemistry at the end of the DNA probe. HyBeacons® are an example of this type of probe.

Target Nucleic Acids and Primers

In accordance with the present invention, oligonucleotide primers and probes are used in the methods described herein to amplify and detect target nucleic acids such as all or a portion of a marker gene specific to Staphylococcus aureus in addition to all or a portion of the mecA gene, and the mecC gene. In one embodiment, the method involves employing primer pairs specifically directed to spa, mecA and mecC including fragments of any or all of these genes.

In addition, primers can also be used to amplify one or more control nucleic acid sequences.

The target nucleic acids described herein may be detected individually or in a multiplex format, utilizing individual labels for each target. In a particular embodiment, a fluorescent labeled primer-probe such as a SCORPION primer-probe is used in a primer pair specifically directed to the mecA gene and contains the same fluorescent label as a fluorescent labeled primer-probe in a primer pair for mecC.

The skilled artisan is capable of designing and preparing primers that are appropriate for amplifying a target nucleic acid in view of this disclosure. The length of the amplification primers for use in the present invention depends on several factors including the nucleotide sequence identity and the temperature at which these nucleic acids are hybridized or used during in vitro nucleic acid amplification. The considerations necessary to determine a preferred length for an amplification primer of a particular sequence identity are well known to the person of ordinary skill in the art.

Designing oligonucleotides to be used as hybridization probes can be performed in a manner similar to the design of primers. As with oligonucleotide primers, oligonucleotide probes usually have similar melting temperatures, and the length of each probe must be sufficient for sequence-specific hybridization to occur but not so long that fidelity is reduced during synthesis. Oligonucleotide probes are generally 15 to 60 nucleotides in length.

In some embodiments, a mix of primers is provided having degeneracy at one or more nucleotide positions. Degenerate primers are used in PCR where variability exists in the target nucleic acid sequence, i.e. the sequence information is ambiguous. Typically, degenerate primers will exhibit variability at no more than about 4, no more than about 3, preferably no more than about 2, and most preferably, no more than about 1 nucleotide position within the primer.

A target nucleic acid may be a gene that is amplified in full. Alternatively, in some embodiments, a target nucleic acid is a fragment or segment of a gene. The fragment may be derived from any region of the full sequence, but fragment length in accordance with the present methods is typically at least 30, at least 50, at least 75, at least 100, at least 150, at least 200, at least 250 or at least 300 nucleotides. As will be understood by one of skill in the art, the size and location of the particular target nucleic acid will control the selection of the amplification primers and vice versa.

Specific primers, probes and primer-probes for amplification and detection of all or a fragment of a marker gene specific for S. aureus include those directed to sequences present in S. aureus, but absent from other Staphylococcus species. Examples of specific marker genes include, but are not limited to spa, agr, ssp protease, sir, sodM, cap, coa, alpha hemolysin, gamma hemolysin, femA, Tuf, sortase, fibrinogen binding protein, clfB, srC, sdrD, sdrE, sdrF, sdrG, sdrH, NAD synthetase, sar, sbi, rpoB, gyrase A, and orfX. The detection of a *S. aureus*-specific gene helps to distinguish a sample containing *S. aureus* from one that may contain other less pathogenic species or strains, e.g. *S. epidermidis*. A suitable marker gene is the 1.55 kb spa gene (see, for example, GenBank Accession No. NC_002952, range 125378-123828). Exemplary primer and labeled primer-probe sequences for amplifying and detecting spa include:

```
S. aureus spa primer 1:
                              (SEQ ID NO: 1)
5'd CTTGATAAAAAGCATTTTGTTGAGCTTCA 3'

S. aureus spa primer 2:
                              (SEQ ID NO: 3)
5' TGCATCTGTAACTTTAGGTACATTA 3'

S. aureus spa labeled primer-probe:
                        (SEQ ID NOs: 2 and 3)
5'd BHQ-1-agcggtGCAGCAGGTGTTACGCCACCgc-T(FAM)-
Spacer18-TGCATCTGTAACTTTAGGTACATTA 3'
```

The skilled artisan will understand that other primers, probes, and primer-probes (including other SCORPION primer-probes) may be used.

Specific primers and probes are selected to amplify and detect a fragment of the 2.0 kb mecC gene (see, for example, GenBank Accession No. FR821779, range 36219-36322). Exemplary primer and labeled primer-probe sequences for amplifying and detecting mecC include:

```
mecAh Primer 1:
                              (SEQ ID NO: 4)
5'd TCACCGATTCCCAAATCTTGC 3' mecAh Primer 2:
                              (SEQ ID NO: 6)
5' AAGCAAGCAATAGAATCATCAGACA 3' mecAh labeled primer-probe:
                        (SEQ ID NOs: 5 and 6)
5'd CFR610-acgtgCCTAATGCTAATGCAATGCGGGCAcgt-
BHQ-2-Spacer 18-AAGCAAGCAATAGAATCATCAGACA 3'
```

The skilled artisan will understand that other primers, probes, and primer-probes (including other SCORPION™ primer-probes) directed to mecC may be used.

Specific primers and probes are selected to amplify and detect a fragment of the 2.0 kb mecA gene (see, for example, GenBank Accession No. X52593, range 1491-1519). Exemplary primer and labeled primer-probe sequences for amplifying and detecting mecA include:

```
mecA Primer 1:
                              (SEQ ID NO: 7)
5'd TCTTCACCAACACCTAGTTTTTTCA 3' mecA Primer 2:
                              (SEQ ID NO: 9)
5' GGTAATATCGACTTAAAACAAGCAATAGA 3' mecA labeled primer-probe:
                        (SEQ ID NOs: 8 and 9)
5'd CFR610acgcggcCTTACTGCCTAATTCGAGT
GCTACTCTAGCgccgcgt-BHQ-2-Spacer18
GGTAATATCGACTTAAAACAAGCAATAGA 3'
```

Accordingly, qualitative detection and differentiation of *S. aureus* and methicillin-resistant *S. aureus* using the disclosed method may utilize primer pairs that comprise a primer-probe and real-time PCR for amplification and detection of the *S. aureus* specific gene spa, and the methicillin-resistance genes mecA and mecC on a direct amplification disc with an integrated cycler system. With this method, target nucleic acid, such as target genomic DNA, is specifically amplified and simultaneously detected by fluorescent-labeled probes in the same reaction. The primer-probe of the spa primer pair may comprise a fluorescein amidite (e.g., FAM) label and each of the primer-probes of the mecA and mecC primer pairs may comprise a xanthene dye that fluoresces in the red region of the visible spectrum (e.g. CFR610).

Algorithms

Upon subjecting the sample-reaction mixtures to real time PCR, and detecting and measuring the fluorescence signals associated with the amplified genes, the methods of the present invention further provide that the presence or absence of MRSA is determined by using MRSA algorithm, which provides the final results by matching cycle threshold (Ct) from the amplified target nucleic acid sequences. Preferably, the mecA and mecC target nucleic acids are amplified using a primer-probe labeled with a xanthene dye that fluoresces in the red region of the visible spectrum such as CFR610, and the spa target nucleic acid sequence is amplified using a primer-probe that is labeled with a fluorescein amidite fluorophore such as FAM. Thus, the signals of mecA and/or mecC (designated "Ct of mecA_C (CFR610 channel)" below) are from the xanthene dye and the signal of spa (designated "Ct of SA (FAM channel)" below) is from the fluorescein amidite fluorophore.

The MRSA algorithm dictates:

| Interpretation (presence in sample) | S. aureus specific gene (e.g., spa) | mecA and/or mecC | Internal control (IPC) | Ct. Compare |
|---|---|---|---|---|
| S. aureus (SA) | Detected | Not Detected | N/A | |
| Negative | Not Detected | Not Detected | Detected | |
| Negative | Not Detected | Detected | N/A | |
| MRSA | Detected | Detected | N/A | "SA"="mecA_C"+−1.9 |
| MRSA | Detected | Detected | N/A | "SA"!="mecA_C"+−1.9 AND "mecA_C"+ 1.9<"SA" |
| SA and methicillin resistance | Detected | Detected | N/A | "SA"!="mecA_C"+−1.9 AND "SA"+ 1.9<"mecA_C" |

-continued

| Interpretation (presence in sample) | S. aureus specific gene (e.g., spa) | mecA and/or mecC | Internal control (IPC) | Ct. Compare |
|---|---|---|---|---|
| Invalid | Not Detected | Not Detected | Not Detected | |

Accordingly, the presence or absence of MRSA in a sample can be determined based on the following scenarios:

(1) MRSA is determined to be present in said biological sample when a fluorescent signal is detected for both the S. aureus specific gene (FAM signal) and the mecA and/or mecC genes (CFR610 signal), and if:

(a) Ct of SA (FAM channel)–Ct of mecA_C (CFR610 channel)≤1.9 (i.e., the cycle threshold from the S. aureus specific target nucleic acid sequence (for example, spa) minus the cycle threshold from the mecA and/or mecC target nucleic acid sequences≤1.9), or if (b) Ct of SA (FAM channel)–Ct of mecA_C (CFR610 channel)>1.9, and Ct of mecA_C (CFR610 channel)+1.9<Ct of SA (FAM channel) (i.e., the cycle threshold from the S. aureus specific target nucleic acid sequence (for example, spa) minus the cycle threshold from the mecA and/or mecC target nucleic acid sequences>1.9 and the cycle threshold from the mecA and/or mecC target nucleic acid sequences plus 1.9<the cycle threshold from the S. aureus specific target nucleic acid sequence)

(2) S. aureus and at least one methicillin resistance gene are determined to be present in the sample when a fluorescent signal is detected for both the S. aureus specific target nucleic acid sequence (FAM signal) and the mecA and/or mecC target nucleic acid sequences (CFR610 signal) and if Ct of SA (FAM channel)–Ct of mecA_C (CFR610 channel)<1.9, and Ct of SA (FAM channel)+1.9<Ct of mecA_C (CFR610 channel) (i.e., the cycle threshold from the S. aureus specific target nucleic acid sequence minus the cycle threshold from the mecA and/or mecC target nucleic acid sequences<1.9, and the cycle threshold from the S. aureus specific target nucleic acid sequence plus 1.9<cycle threshold from the mecA and/or mecC target nucleic acid sequences).

In such a case, S. aureus is present in the sample as well as a methicillin resistance gene, but that methicillin resistance gene could be coming from the S. aureus or from a coagulase negative Staphylococcus in the same sample.

(3) A sample with a detectable signal (FAM) for the S. aureus specific target nucleic acid sequence but no detectable CFR610 signal for mecA and/or mecC is interpreted as containing S. aureus but not MRSA.

(4) If a signal for the S. aureus specific target nucleic acid sequence (FAM signal) is not detected and a signal for mecA or mecC (CFR610) is also not detected, then the sample is interpreted as S. aureus and MRSA negative.

Kits

Kits comprising oligonucleotides which may be primers or primer-probes for performing amplifications as described herein to determine the presence or absence of MRSA in a biological sample also are provided by the present invention. A kit of the present invention may further include oligonucleotides that may be used as probes to detect amplified nucleic acid, and/or one or more restriction enzymes for digesting non-target nucleic acid to increase detection of target nucleic acid by the oligonucleotide primers.

In some embodiments, a kit comprises (i) a first primer pair that specifically hybridizes under stringent conditions to a segment of a target marker gene specific for Staphylococcus aureus, (ii) a second primer pair that specifically hybridizes under stringent conditions to a segment of a target mecC gene, and (iii) a third primer pair that specifically hybridizes under stringent conditions to a segment of a target mecA gene.

The first primer pair may specifically hybridize to the spa gene and may consist of an oligonucleotide comprising SEQ ID NO:1 and either an oligonucleotide comprising SEQ ID NO:3 or a primer-probe consisting of SEQ ID NOs: 2 and 3. The second primer pair may consist of an oligonucleotide comprising SEQ ID NO:4 and either an oligonucleotide comprising SEQ ID NO:6 or a primer-probe consisting of SEQ ID NOs: 5 and 6. The third primer pair may consist of an oligonucleotide comprising SEQ ID NO:7 and either an oligonucleotide comprising SEQ ID NO:9 or a primer-probe consisting of SEQ ID NOs: 8 and 9.

The kit additionally may comprise an assay definition scan card and/or instructions such as printed or electronic instructions for using the oligonucleotides in an assay. In some embodiment, the kit comprises instructions for analyzing a biological sample to determine the presence or absence of MRSA. In some embodiments, a kit comprises an amplification reaction mixture or an amplification master mix. Reagents included in the kit may be contained in one or more containers, such as a vial.

Primers, probes, and/or primer-probes specific for amplification and detection of DNA internal control may be included in the amplification master mix as the target primer pairs to monitor potential PCR inhibition. Reagents necessary for amplification and detection of targets and internal control may be formulated as an all-in-one amplification master mix, which may be provided as single reaction aliquots in a kit.

EXAMPLES

Example 1

A nasal swab sample is obtained from an individual in appropriate collection device. 50 µl of unprocessed nasal swab sample is loaded directly into a sample well of wedge 1 of a SIMPLEXA Direct Amplification Disc (Focus Diagnostics, Inc., Cypress, Calif., USA) without a separate front-end specimen preparation step. 50 µl of Amplification master mix is pipetted into the reaction well of wedge 1 of the disc, wherein the amplification master mix contains PCR buffer, DNA polymerase, dNTPs, magnesium chloride, potassium chloride, ammonium sulfate, primers consisting of SEQ ID NOs: 1, 2 and 3, 4, 5 and 6, 7 and 8 and 9 and an internal control DNA fragment and a primer pair specific to the control fragment. The primers consisting of SEQ ID NOs: 2 and 3, 5 and 6 and 8 and 9 are SCORPION primer-probes and are labeled with FAM (SEQ ID NOs: 2 and 3) or CFR610 (SEQ ID NOs: 5 and 6, and 8 and 9).

The wedge is sealed with foil and the Direct Amplification Disc is then inserted into a 3M™ Integrated Cycler (3M, St.

Paul, Minn., USA) and RT-PCR commences in the cycler. The PCR cycling conditions include the following steps: i) sample pre-heat at 97° C., 480 seconds, 1 cycle ii) polymerase activation at 97° C., 120 seconds, 1 cycle iii) Denaturation at 97° C., 10 seconds and annealing at 58° C., 30 seconds for 37 cycles.

Target genomic DNA is specifically amplified and simultaneously detected by fluorescent-labeled primer-probes in the same reaction. The presence of MRSA is determined by the following MRSA algorithm, which provides the final results by matching cycle threshold (Ct) in the FAM and CFR610 channels:

A sample with signal in FAM and CFR610 channels is interpreted as MRSA if:
1) Ct of SA (FAM channel)−Ct of mecA_C (CFR610 channel)≤1.9, or
2) Ct of SA (FAM channel)−Ct of mecA_C (CFR610 channel)>1.9 and Ct of mecA_C (CFR610 channel)+1.9<Ct of SA (FAM channel)

A sample with signal in FAM and CFR610 channels is interpreted as SA, meth resist if: 1) Ct of SA (FAM channel)−Ct of mecA_C (CFR610 channel)<1.9 and Ct of SA (FAM channel)+1.9<Ct of mecA_C (CFR610 channel)

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

The invention claimed is:

1. A method for determining the presence or absence of methicillin-resistant Staphylococcus aureus (MRSA) in a biological sample comprising:
   (a) contacting the biological sample with:
      (i) a first primer pair that specifically hybridizes under stringent conditions to a segment of a target nucleic acid specific for Staphylococcus aureus, if present, wherein one primer of the first primer pair comprises SEQ ID NO:2,
      (ii) a second primer pair that specifically hybridizes under stringent conditions to a segment of a target mecC nucleic acid if present, and
      (iii) a third primer pair that specifically hybridizes under stringent conditions to a segment of a target mecA nucleic acid, if present,
   to produce a reaction-sample mixture, wherein at least one primer of each primer pair is associated with a fluorophore label,
   (b) subjecting the reaction-sample mixture to real-time polymerase chain reaction (PCR) conditions under which each of the target nucleic acids present in the biological sample is amplified to produce a fluorescent signal,
   (c) measuring the amount of fluorescent signal produced by each fluorophore, and
   (d) determining the presence or absence of MRSA by comparing the amount of fluorescence from the S. aureus specific target nucleic acid and the mecA and mecC target nucleic acids.

2. The method of claim 1, wherein one primer of each primer pair is a primer-probe that comprises a probe sequence element at the 5' end of the primer, wherein the probe sequence element further comprises a fluorophore and a quencher, and wherein the fluorophore of the mecA primer and the fluorophore of the mecC primer are identical.

3. The method of claim 2, wherein the primer-probe of the first primer pair comprises a fluorescein amidite fluorophore and the primer-probes of the second and third primer pairs comprise a xanthene dye that fluoresces in the red region of the visible spectrum.

4. The method of claim 1, wherein all primer pairs are contained together in an amplification master mix further comprising DNA polymerase, dNTPs and PCR buffer prior to contacting with the biological sample.

5. The method of claim 1, wherein step (a) further comprises contacting the biological sample with a fourth primer pair that specifically hybridizes under stringent conditions to a segment of a control target nucleic acid.

6. The method of claim 1 wherein
   (a) the first primer pair consists of a first primer comprising SEQ ID NO:1 and a second primer comprising SEQ ID NO: 2; and/or
   (b) the second primer pair consists of a first primer comprising SEQ ID NO:4 and a second primer comprising SEQ ID NO:6; and/or
   (c) the third primer pair consists of a first primer comprising SEQ ID NO:7 and a second primer comprising SEQ ID NO:9.

7. The method of claim 6, wherein the primer-probe of the first primer pair comprises a fluorescein amidite fluorophore and the primer-probes of the second and third primer pairs comprise a xanthene dye that fluoresces in the red region of the visible spectrum.

8. A detection method comprising:
(a) contacting a biological sample with:
(i) a first primer pair that specifically hybridizes under stringent conditions to a segment of a target nucleic acid specific for *Staphylococcus aureus*, if present, wherein one primer of the first primer pair comprises SEQ ID NO:2,
(ii) a second primer pair that specifically hybridizes under stringent conditions to a segment of a target mecC nucleic acid if present, and
(iii) a third primer pair that specifically hybridizes under stringent conditions to a segment of a target mecA nucleic acid, if present,
to produce a reaction-sample mixture, wherein at least one primer of each primer pair is associated with a fluorophore label,
(b) subjecting the reaction-sample mixture to real-time polymerase chain reaction (PCR) conditions under which each of the target nucleic acids present in the biological sample is amplified to produce a fluorescent signal, and
(c) measuring the amount of fluorescent signal produced by each fluorophore.

9. The method of claim 8, wherein the first primer pair consists of a first primer comprising SEQ ID NO:1 and a second primer comprising SEQ ID NO: 2.

10. The method of claim 8, wherein the second primer pair consists of a first primer comprising SEQ ID NO:4 and a second primer comprising SEQ ID NO:6.

11. The method of claim 8, wherein the third primer pair consists of a first primer comprising SEQ ID NO:7 and a second primer comprising SEQ ID NO:9.

12. The method of claim 8, wherein one primer of each primer pair is a primer-probe that comprises a probe sequence element at the 5' end of the primer, wherein the probe sequence element further comprises a fluorophore and a quencher, and wherein the fluorophore of the mecA primer and the fluorophore of the mecC primer are identical.

13. The method of claim 12, wherein the primer-probe of the first primer pair comprises a fluorescein amidite fluorophore and the primer-probes of the second and third primer pairs comprise a xanthene dye that fluoresces in the red region of the visible spectrum.

14. The method of claim 13, wherein the primer-probe of the first primer pair comprises a probe sequence of SEQ ID NO: 2 and a primer sequence of SEQ ID NO: 3 arranged 5' to 3'.

15. The method of claim 13, wherein primer-probe of the second primer pair comprises a probe sequence of SEQ ID NO: 5 and a primer sequence of SEQ ID NO: 6 arranged 5' to 3'.

16. The method of claim 13, wherein primer-probe of the third primer pair comprises a probe sequence of SEQ ID NO: 8 and a primer sequence of SEQ ID NO: 9 arranged 5' to 3'.

17. The method of claim 13, wherein:
(i) MRSA is determined to be present in the biological sample when a fluorescent signal is detected for both the *S. aureus*-specific target nucleic acid and the mecA and/or mecC nucleic acids and
(1) the cycle threshold (Ct) from the *S. aureus*-specific target nucleic acid minus the Ct from the mecA and/or mecC nucleic acids≤1.9 and ≥−1.9, or
(2) the Ct from the *S. aureus*-specific target nucleic acid minus the Ct from the mecA and/or mecC nucleic acids>1.9;
(ii) *S. aureus* and a methicillin-resistance gene are determined to be present in the biological sample when a Ct is detected for both the *S. aureus*-specific target nucleic acid and the mecA and/or mecC nucleic acids, and the Ct from the *S. aureus*-specific target nucleic acid plus 1.9<the Ct from the mecA and/or mecC nucleic acids; or
(iii) *S. aureus* is determined to be present and MRSA is determined to be absent in the biological sample if a fluorescent signal is detected for the *S. aureus*-specific target nucleic acid sequence but no fluorescent signal is detected for mecA and mecC.

\* \* \* \* \*